United States Patent [19]

Boyle et al.

[11] Patent Number: 4,999,364
[45] Date of Patent: Mar. 12, 1991

[54] AZOLE DERIVATIVES

[75] Inventors: Francis T. Boyle; Zbigniew S. Matusiak, both of Cheshire, England

[73] Assignee: Imperial Chemical Industries PLC, London, England

[21] Appl. No.: 390,245

[22] Filed: Aug. 7, 1989

[30] Foreign Application Priority Data

Aug. 8, 1988 [GB] United Kingdom ................. 8818791

[51] Int. Cl.$^5$ .................... C07D 401/10; A61K 31/44
[52] U.S. Cl. ........................................ 514/340; 71/90; 71/92; 546/276; 546/278; 546/255; 546/256; 544/333; 544/242; 548/336; 548/266.6; 514/341; 514/332; 514/333; 514/256; 514/383; 514/396; 514/397
[58] Field of Search ........................ 546/276; 514/340; 71/92

[56] References Cited

FOREIGN PATENT DOCUMENTS 299683  1/1989  European Pat. Off. ............ 546/276
1589852 5/1981 United Kingdom .
1601423 10/1981 United Kingdom .

Primary Examiner—Jane T. Fan
Attorney, Agent, or Firm—Cushman, Darby & Cushman

[57] ABSTRACT

Azole derivatives of the formulas

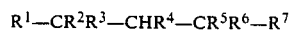

$R^1$—$CR^2R^3$—$CHR^4$—$CR^5R^6$—$R^7$ are described;
wherein $R^1$ is a heterocyclyl radicla selected from 1,2,4-triazolyl, optionally-substituted imidazolyl, pyridyl and pyrimidinyl radicals; $R^2$ and $R^3$, which may be the same or different, are each a hydrogen atom or a 1-6C alkyl radical; $R^5$ and $R^6$, which may be the same or different, are each a hydrógen or fluorine atom or a 1-6C alkyl radical; one of $R^4$ and $R^7$ is a 2-pyridyl or 2-thienyl radical, optionally bearing one or more substituents selected from halogen atoms, cyano radicals and 1-4C halogenoalkyl and halogenoalkoxy radicals, and the other of $R^4$ and $R^7$ is a 4-cyanophenyl radical or a 2-pyridyl or 2-thienyl radical optionally substituted as defined above. Processes for their preparation are described, as is their use as aromatase inhibitors, for example in the treatment of cancer, as plant antifungal agents or as plant growth regulatory agents.

9 Claims, No Drawings

AZOLE DERIVATIVES

This invention relates to azole derivatives possessing aromatase inhibitory, plant antifungal and plant growth regulatory activity, and more particularly it relates to azolylalkane derivatives.

Aromatase is an enzyme which effects aromatisation of ring A in the metabolic formation of various steroid hormones. Various cancers, for example breast cancer, are dependent upon circulating steroid hormones which have an aromatic ring A. Such cancers can be treated by surgical removal of the source of ring A aromatised steroid hormones, for example by the combination of oophorectomy and adrenalectomy. An alternative way of obtaining the same effect is by administering a chemical compound which inhibits the metabolic aromatisation of the non-aromatic steroid precursors of the aromatised steroid hormones, and the novel compounds of this invention are useful for this purpose.

Thus, according to the invention, there is provided an azole derivative of the formula

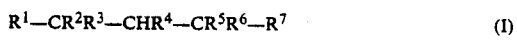

wherein $R^1$ is a heterocyclyl radical selected from 1,2,4-triazolyl, optionally-substituted imidazolyl, pyridyl and pyrimidinyl radicals; $R^2$ and $R^3$, which may be the same or different, are each a hydrogen atom or a 1-6 C alkyl radical; $R^5$ and $R^6$, which may be the same or different, are each a hydrogen or fluorine atom or a 1-6 C alkyl radical; one of $R^4$ and $R^7$ is a 2-pyridyl or 2-thienyl radical, optionally bearing one or more substituents selected from halogen atoms, cyano radicals and 1-4 C halogenoalkyl and halogenoalkoxy radicals, and the other of $R^4$ and $R^7$ is a 4-cyanophenyl radical or a 2-pyridyl or 2-thienyl radical optionally substituted as defined above; and, for those compounds which contain a basic nitrogen atom, the pharmaceutically or veterinarily acceptable salts thereof.

A suitable value for the heterocyclyl radical $R^1$ is, for example, a 1,2,4-triazol- 1-yl, 1-imidazolyl, 5-cyano, 5-methyl- or 5-trifluoromethyl-1-imidazolyl, 3-pyridyl or 5-pyrimidinyl radical.

A suitable value for any of $R^2$, $R^3$, $R^5$ or $R^6$, when any of them is a 1-6 C alkyl radical is, for example, a methyl, ethyl, propyl, isopropyl, butyl, isobutyl, sec-butyl, tert-butyl, pentyl or hexyl radical, and of these methyl and ethyl are preferred.

A suitable value for an optional halogen substituent in $R^4$ or $R^7$ is, for example, a fluorine, chlorine or bromine atom, and of these fluorine and chlorine are preferred.

A suitable value for an optional 1-4 C halogenoalkyl or halogenoalkoxy substituent in $R^4$ or $R^7$ is, for example, a trifluoromethyl, chlorodifluoromethyl, 1,2,2- or 2,2,2-trifluoroethyl, 2,2,3,3,3-pentafluoropropyl, 4,4,4-trifluorobutyl, trifluoromethoxy, 2,2,2-trifluoroethoxy or 4,4,4-trifluorobutoxy radical, and of these trifluoromethyl and trifluoromethoxy are preferred.

A suitable pharmaceutically or veterinarily acceptable salt is, for example, the hydrochloride, nitrate, sulphate, phosphate, acetate, lactate, citrate, maleate or fumarate.

The carbon atom bearing the substituents $R^1$, $R^2$ and $R^3$, the carbon atom bearing the substituent $R^4$, and the carbon atom bearing the substituents $R^5$, $R^6$ and $R^7$, may each be asymmetrically substituted, so that the compound of the formula I may exist in racemic or optically active forms. It is common general knowledge in the art how such a racemate may be resolved into diastereoisomers, or how such diastereoisomers may be synthesized, and their aromatase inhibitory activity determined.

A preferred group of compounds of the invention comprises those azole derivatives of the formula I wherein $R^4$ or $R^7$ bears one or more substituents selected from fluorine and chlorine atoms and cyano, trifluoromethyl and trifluoromethoxy radicals.

Particular preferred compounds of the invention are 6-[2-(4-cyanophenyl)-3-(1,2,4 triazol 1-yl)propyl]-nicotinonitrile and 4-[1-(1,2,4-triazol-1-ylmethyl)-2-(5-trifluoromethyl]pyrid-2-yl)ethyl]benzonitrile.

The azole derivatives of the invention may be manufactured by processes known per se for the manufacture of chemically analogous compounds. Thus, the following processes comprise a further feature of the invention, wherein $R^1$, $R^2$, $R^3$, $R^4$, $R^5$-$R^6$ and $R^7$ have the meanings defined above, unless otherwise stated:

(a) for those compounds wherein $R^5$ is a hydrogen atom, the hydrogenation of a olefinic compound of the formula II

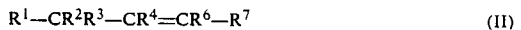

(b) for those compounds wherein $R^2$ is a hydrogen atom, the hydrogenation of an olefinic compound of the formula III

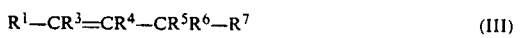

(c) the reaction of a compound of the formula IV

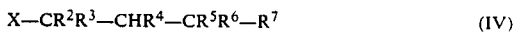

wherein X is a known leaving group, with a heterocyclic compound of the formula $R^1H$ or with an alkali metal salt thereof.

In processes (a) and (b), the hydrogenation is preferably carried out with gaseous hydrogen in the presence of a metal catalyst such as palladium-on-carbon, platinum oxide or Raney nickel. The hydrogenation is preferably carried out at ambient temperature until uptake of hydrogen ceases.

In process (c), a suitable known leaving group X is, for example, a mesyl, tosyl or bromo group, and a suitable alkali metal salt of the heterocyclic compound of the formula $R^1H$ is, for example, a sodium salt.

The olefinic compound of the formula II, which is used as the starting material in process (a) above, may be obtained in conventional manner, for example by brominating a ketone of the formula $R^2R^3CH\text{-}CO\text{-}R^4$ to form an alpha-bromoketone of the formula $Br\text{-}CR^2R^3\text{-}CO\text{-}R^4$, which is then reacted with a heterocyclic compound $R^1H$ or a reactive derivative thereof to form a ketone of the formula $R^1\text{-}CR^2R^3\text{-}CO\text{-}R^4$. This ketone is then reacted with a Wittig reagent of the formula Q-$CHR^6\text{-}R^7$, wherein Q is a triphenylphosphine halide $(Hal^{31}.Ph_3P^+\text{-})$ or dialkylphosphono $[(R^8O)_2PO\text{-}]$ radical, to give the required olefinic starting material.

Alternatively, the ketone $R^1\text{-}CR^2R^3\text{-}CO\text{-}R^4$ wherein $R^1$ is a 1,2,4-triazol-1-yl radical may be obtained by reacting the precursor alpha-bromoketone with 4-amino-1,2,4-triazole, followed by removal of the amino group from the product so obtained, by reaction with sodium nitrite.

The olefinic compound of the formula III which is used as the starting material in process (b) above may be obtained similarly by reacting a ketone of the formula $R^4$-CO-$CR^5R^6$-$R^7$ with a Wittig reagent of the formula $R^1$-$CHR^2$-Q.

The compound of the formula IV which is used as the starting material for process (c) may be obtained by reacting a nitrile derivative of the formula $R^4$-$CH_2$-CN with a compound of the formula X-$CR^5R^6$-$R^7$ to give a nitrile of the formula NC-$CHR^4$-$CR^5R^6$-$R^7$ which is then selectively hydrolysed and esterified, for example with ethanol, to give an ester of the formula $C_2H_5O$-CO-$CHR^4$-$CR^5R^6$-$R^7$. This ester is then reduced to the corresponding alcohol $HO.CH_2$-$CHR^4$-$CR^5R^6$-$R^7$, for example with lithium aluminium hydride, and the alcohol is converted to the required starting material IV by reaction with mesyl or tosyl chloride or phosphorus oxybromide.

As indicated above, the compounds of the invention are useful as aromatase inhibitors. Aromatase inhibition may be demonstrated by the following tests:

DEMONSTRATION OF ACTIVITY IN VITRO

Aromatase inhibitory activity was measured using the enzyme present in the microsomal fraction of human term placenta, as described by Ryan, J. Biol. Chem. 234, 268, 1959. Enzyme activity was determined by measuring the amount of tritiated water released from 0.5 micromolar ($1\beta,2\beta$-$^3$H)testosterone after 20 minutes incubation at 37°. The method used was essentially that described by Thomson and Siiteri, J. Biol. Chem. 249, 5364, 1974 except that testosterone was used in place of androstenedione. Test compounds were dissolved in dimethylsulphoxide (DMSO) to achieve final concentrations of 2, 0.2 or 0.02 $\mu$g/ml. The reaction was started by the addition of 50 $\mu$l of microsome suspension to 50 $\mu$l of a solution containing substrate (testosterone) and cofactors (NADPH glucose-6-phosphate and glucose-6-phosphate dehydrogenase) and either DMSO alone or a DMSO solution of test compound. Each concentration of test compound was tested in triplicate. The reaction was stopped by the addition of 200 $\mu$l of a 5% (w/v) suspension of charcoal in 0.5% (w/v) solution of Dextran T70 in water. After 1 hour the charcoal was precipitated by centrifugation and 150 $\mu$l of supernatant removed and the amount of tritiated water present determined using a liquid scintillation counter. The number of counts in supernatant from incubations containing test compound expressed as a percentage of the counts in supernatant from incubations containing only DMSO was taken as the degree of enzyme inhibition achieved by the test compound.

DEMONSTRATION OF ACTIVITY IN VIVO

Activity in vivo was demonstrated in terms of ovulation inhibition in female rats. Daily vaginal smears were taken from rats housed under controlled lighting (lights on 06.00 hr to 20.00 hr) and those having a vaginal smear pattern consistent with 4-day ovarian cycles were selected. To these rats a single dose of test compound was given either at 16.00 hr on Day 2 of the cycle or at 12.00 hr on Day 3 of the cycle. The rats were then killed in the morning following Day 4 of the cycle—approximately 64 hours after Day 2 treatments or approximately 46 hours after Day 3 treatments—and the presence or absence of eggs in the fallopian tubes determined. The presence of eggs indicates that the rats have ovulated.

Without treatment more than 95% of rats with 4-day ovarian cycles are found to have ovulated at the time of the post-mortem examination. At an effective dose, aromatase inhibitors prevent ovulation, i.e. no eggs are found in the fallopian tubes.

Thus, according to a further feature of the invention, there is provided a pharmaceutical or veterinary composition comprising an azole derivative, as defined above, together with a pharmaceutically or veterinarily acceptable diluent or carrier.

The pharmaceutical or veterinary composition of the invention may be a conventional formulation for oral or parenteral administration, for example a tablet, a capsule, an emulsion or an aqueous or oily solution or suspension. The composition may contain conventional pharmaceutical excipients, and may be manufactured by conventional pharmaceutical techniques.

Preferred pharmaceutical or veterinary compositions of the invention are tablets and capsules containing from 1 to 100, preferably 5 to 50 mg. of a compound of the invention.

The compounds of the invention also possess antifungal properties which are useful in combatting a wide variety of plant fungal diseases, and plant growth regulating properties.

The compounds can move acropetally when applied to the plant tissue, and can also be volatile enough to be active in the vapour phase against fungi on plants.

The compounds may be used as such for plant fungicidal or plant growth regulating purposes but are more conveniently formulated into compositions for such usage. The invention thus provides also a plant fungicidal composition comprising an azole derivative of general formula I and a non-pharmaceutical carrier or diluent.

The invention also provides a method of combatting fungal diseases in a plant, which method comprises applying to the plant, to seed of the plant or to the locus of the plant or seed an azole derivative of the formula I.

The invention also provides a method of regulating plant growth which comprises applying to the plant, to seed of the plant or to the locus of the plant or seed an azole derivative of the formula I.

The compound can be applied in a number of ways, for example it can be applied, formulated or unformulated, directly to the foliage of a plant, to seeds or to the medium in which plants are growing or are to be planted, or it can be sprayed on, dusted on or applied as a cream or paste formulation, or it can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged, and the choice of a suitable conventional composition, and the method by which such a composition may be manufactured, are apparent to those skilled in the art.

The plant fungicidal and plant growth regulating compositions of this invention can comprise also other compound(s) having biological activity, e.g. compounds having similar or complementary fungicidal or plant growth regulating activity or compounds having herbicidal or insecticidal activity.

The invention is illustrated but not limited by the following Examples. Temperatures given are in degrees Celsius:

EXAMPLE 1

A mixture of 6-[-2-(4-cyanophenyl)-3-(1,2,4-triazol-1-yl)prop-1-enyl]nicotinonitrile (0.2 g) and 10% by weight palladium-on-carbon (0.1 g) in ethyl acetate (20 ml) was stirred rapidly under an atmosphere of hydrogen at atmospheric pressure for 1 h. The mixture was filtered and the filtrate was evaporated to dryness. The residue was triturated with diethyl ether to give a white solid, which was filtered off, washed with more ether (10 ml) and dried to give 6-[-2-(4-cyanophenyl)-3-(1,2,4-triazol-1-yl)propyl]nicotinonitrile, m.p. 98°.

The starting material used in the above process was obtained as follows:

(1) A solution of 4-bromoacetylbenzonitrile (24 g) and 4-amino-1,2,4-triazole (9 g) in acetonitrile (150 ml) was heated under reflux for 1.5 h. The solvent was evaporated under reduced pressure and a solution of concentrated hydrochloric acid (38 ml) in water (300 ml) was added. The solution was cooled to 10°, and sodium nitrite (13.6 g) was added in portions over 7 minutes. The reaction mixture was then cooled to 5°, and stirred for 30 minutes. The pH was adjusted to 8 by the addition of solid potassium carbonate, and 4-(1,2,4-triazol-1-ylacetyl)benzonitrile crystallised as a white solid, which was filtered off and washed with ethyl acetate, then diethyl ether, m.p. 208°-211°.

(2) A mixture of 6-methylnicotinonitrile (4.15 g) and 3-chloroperbenzoic acid (8.3 g) in dichloromethane (200 ml) was stirred under an argon atmosphere at room temperature for 16h. The dichloromethane was evaporated under reduced pressure and the residue purified by flash column chromatography on silica (K60), using ethyl acetate and then methanol: dichloromethane (1:9 by volume) as eluting solvent to give 5-cyano-2-methylpyridine-1-oxide, mp 133.5°.

A solution of phosphoryl chloride (6.5 g) in dichloromethane (20 ml) was added to a mixture of the above pyridine-1-oxide (4.4 g) and triethylamine (4.3 g) in dichloromethane (60 ml). After the addition was completed the reaction mixture was gently refluxed for 15 mins, cooled and washed with water (30 ml). The organic layer was separated, dried over anhydrous sodium sulphate and evaporated to dryness. The residue was purified by flash column chromatography on silica (K60) using ethyl acetate: toluene (1:9 by volume) as eluting solvent, to give 6-chloromethylnicotinonitrile.

A mixture of this chloromethyl compound (2 g) and triphenylphosphine (4.11 g) in acetonitrile (80 ml) was stirred and heated under reflux for 24 h. The acetonitrile was avaporated under reduced pressure and ethyl acetate (200 ml) added to the residue. The solid was filtered and dried to give (4-cyanopyridyl)-triphenylphosphonium chloride, mp 267°.

(3) A suspension of (4-cyanopyridyl)triphenylphosphonium chloride (3.85 g), 4 (1,2,4-triazol-1-ylacetyl)-benzonitrile (1.0 g), potassium tert-butoxide (1.1 g) and 18-crown-6 (1,4,7,10,13,16-hexaoxacyclooctadecane, 0.1 g) in dichloromethane (150 ml) was stirred at room temperature for 1 h. Saturated ammonium chloride solution (100 ml) was then added, and the organic layer was separated. The aqueous layer was extracted twice with dichloromethane, and the combined organic extracts were dried and evaporated to dryness, to give the required 6-[2-(4-cyanophenyl)-3-(1,2,4-triazol-1-yl)prop-1-enyl]nicotinonitrile, m.p. 211°.

EXAMPLE 2

The process described in Example 1 was repeated, using 4-]1-(1,2,4-triazol-1ylmethyl)-2-]5-(trifluoromethyl)pyrid-2-yl]vinyl]benzonitrile as starting material, to give 4-[1-(1,2,4-triazol-1-ylmethyl)-2-(5-[trifluoromethyl]pyrid-2-yl)ethyl]-benzonitrile, m.p. 78°.

The starting material used in the above process may be obtained as follows:

A solution of 5-(trifluoromethyl)pyridine-2-carbonitrile (50 g) in hydrochloric acid (10M, 500 ml) was heated under reflux for 16 h. The reaction mixture was then evaporated under reduced pressure to give 5-(trifluoromethyl)pyridine-2-carboxylic acid hydrochloride. A solution of this acid (75 g) and concentrated sulphuric acid (98%, 4 ml) in methanol (500 ml) was heated under reflux for 16 h, cooled and added to a solution of sodium bicarbonate (50 g) in water (200 ml). The methanol was evaporated under reduced pressure and the residue was extracted with diethyl ether (3×200 ml). The extracts were combined, dried and evaporated to dryness to give the ester, methyl 5-(trifluoromethyl) pyridine-2-carboxylate.

A mixture of this ester (47 g) and sodium borohydride (43.5 g) in ethanol was warmed until reflux started. The heating was then removed, the mixture was stirred for 30 minutes, then the ethanol was evaporated under reduced pressure and water (1000 ml) was added. The mixture was extracted with diethyl ether (3×300 ml), and the extracts were combined, dried and evaporated to dryness under reduced pressure to give the alcohol, 5-(trifluoromethyl)pyridine-2-methanol.

A mixture of this alcohol (5.2 g), triethylamine (8.5 ml) and methanesulphonyl chloride (3.36 ml) in dichloromethane (300 ml) was stirred at 0° for 1 h. The reaction mixture was washed with saturated sodium bicarbonate solution (150 ml), dried, and purified by chromatography on a silica column (Merck Art No. 9385), eluting with ethyl acetate/hexane (1:1 by volume). The residue was dissolved in diethyl ether (250 ml) and a solution of ethereal hydrogen chloride was added, to give a precipitate which was filtered off, washed with diethyl ether and dried. On standing at room temperature for 16 h, the solution yielded 2-chloromethyl-5-(trifluoromethyl)pyridine, N.M.R. in deuteriochloroform: $\delta$ 5.05 (2H,s), 8.0 (1H,d), 8.35 (1H,d), 8.9 (1H,s).

A solution of triphenylphosphine (5 g) and 2-chloromethyl-5-(trifluoromethyl)pyridine (5 g) in acetonitrile (100 ml) was heated under reflux for 16 h. The acetonitrile was evaporated under reduced pressure, and ethyl acetate (100 ml) was added to the residue. The solid so obtained was filtered off, washed with ethyl acetate and dried, to give (5-trifluoromethyl-2-pyridylmethyl)triphenylophosphonium chloride, N.M.R. in deuteriochloroform: $\delta$ 7.5 (m), 7.75 (m).

A suspension of (5-trifluoromethyl-2pyridylmethyl)-triphenylphoshonium chloride (2.75 g), 4-(1,2,4-trizol-1-ylacetyl)benzonitrile (1.27 g), potassium tert-butoxide (0.67 g) and 18-crown-6 (0.1 g) in dichloromethane (200 ml) was stirred for 72 h. The reaction mixture was then purified by column chromatography on silica (Merck Art No. 9385), using successively ethyl acetate/hexane (75/25 by volume), ethyl acetate and methanol/dochloromethane (5:95 by volume) as eluant, to give a mixture of the E and Z isomers, m.p. 156° and 105° respectively.

We claim:

1. An azole derivative of the formula

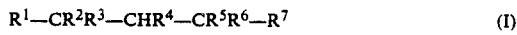
$$R^1—CR^2R^3—CHR^4—CR^5R^6—R^7 \quad (I)$$

wherein $R^1$ is a 1,2,4-triazolyl radical; $R^2$ and $R^3$, which may be the same or different, are each a hydrogen atom or a 1-6 C alkyl radical; $R^5$ and $R^6$, which may be the same or different, are each a hydrogen or fluorine atom or a 1-6 C alkyl radical; one of $R^4$ and $R^7$ is a pyridyl radical which is unsubstituted or substituted by one or more substituents selected from halogen atoms, cyano radicals and 1-4 C halogenoalkyl and halogenoalkoxy radicals, and the other of $R^4$ and $R^7$ is a 4-cyanophenyl radical or, for a compound which contains a basic nitrogen atom, a pharmaceutically or veterinarily acceptable salt thereof.

2. An azole derivative as claimed in claim 1 wherein $R^2$ and $R^3$, which may be the same or different, are each hydrogen or a methyl, ethyl, proply, isopropyl, butyl, isobutyl, sec-butyl, tert-butyl, pentyl or hexyl radical $R^5$ and $R^6$, which may be the same or different, are each a hydrogen or fluorine atom, or a methyl, ethyl, propyl, isopropyl, butyl, isobutyl, sec-butyl, tert-butyl, pentyl or hexyl radical, one of $R^4$ and $R^7$ is a 2-pyridyl radical which is unsubstituted or substituted by one or more substituents selected from fluorine, chlorine and bromine atoms, cyano radicals and trifluoromethyl, chlorodifluoromethyl, 1,2,2- or 2,2,2-trifluoroethyl, 2,2,3,3,3- pentafluoropropyl, 4,4,4,-trifluorobutyl, trifluoromethoxy, 2,2,2-trifluoroethoxy and 4,4,4-trifluorobutoxy radicals, and the other of $R^4$ and $R^7$ is a 4-cyanophenyl radical; or, for a compound which contains a basic nitrogen atom, the hydrochloride, nitrate, sulphate, phosphate, acetate, lactate, citrate, maleate and fumarate thereof.

3. An azole derivative as claimed in claim 1 wherein $R^4$ or $R^7$ bears one or more substituents selected from fluorine and chlorine atoms and cyano, trifluoromethyl and trifluoromethoxy radicals.

4. An azole derivative as claimed in claim 1 which is selected from 6-[2-(4-cyanophenyl)-3-(1,2,4-triazol-1-yl)propyl]nicotinonitrile and 4-]1-(1,2,4-triazol-1-ylmethyl)- 2-(5-[trifluoromethyl]pyrid-2 -yl) ethyl]benzonitrile.

5. A pharmaceutical or veterinary composition comprising an aromatase inhibitory amount of an azole derivative as claimed in claim 1 together with a pharmaceutically or veterinarily acceptable diluent or carrier.

6. A method of inhibiting aromatase which comprises administering to a host in need of such treatment an effective aromatase inhibitory amount of an azole derivative as claimed in claim 1.

7. A plant fungicidal composition comprising an antifungally effective amount of an azole derivative as claimed in claim 1 and a non-pharmaceutical carrier or diluent.

8. A method of combatting fungal diseases in a plant, which method comprises apply to the plant, to seed of the plant or to the locus of the plant or seed an antifungally effective amount of an azole derivative as claimed in claim 1.

9. A method of regulating plant growth which comprises applying to the plant, to seed of the plant, or to the locus of the plant or seed an antifungally effective amount of an azole derivative as claimed in claim 1.

* * * * *